United States Patent [19]

Schwarz

[11] Patent Number: 4,666,698

[45] Date of Patent: May 19, 1987

[54] N-(4-AMINOBENZOYL)-AMINODICAR-BOXYLIC ACIDS FOR STABILIZING TECHNETIUM$^{99m}$ PREPARATIONS, STABILIZED INJECTION PREPARATIONS, AND PROCESSES FOR PRODUCING THEM

[75] Inventor: Alexander Schwarz, Flörsheim am Main, Fed. Rep. of Germany

[73] Assignee: Hoechst Aktiengesellschaft, Fed. Rep. of Germany

[21] Appl. No.: 644,953

[22] Filed: Aug. 28, 1984

[30] Foreign Application Priority Data

Aug. 30, 1983 [DE] Fed. Rep. of Germany ....... 3331159

[51] Int. Cl.$^4$ ...................... A61K 43/00; A61K 49/02
[52] U.S. Cl. ......................................... 424/1.1; 424/9; 534/14
[58] Field of Search ....................... 424/1.1, 9; 534/14

[56] References Cited

U.S. PATENT DOCUMENTS 4,233,284 11/1980 Fawzi ................................. 424/1.1
4,313,928  2/1982 Kato et al. .......................... 424/1.1
4,358,434 11/1982 Tzodikov et al. .................... 424/1.1
4,390,517  6/1983 O'Brien et al. ...................... 424/1.1
4,411,881 10/1983 Tzodikov ............................ 424/1.1
4,427,647  1/1984 Brockas et al. ...................... 424/1.1
4,497,744  2/1985 Fawzi ................................. 424/1.1
4,510,125  4/1985 Grogg et al. ........................ 424/1.1

FOREIGN PATENT DOCUMENTS 1541070 2/1979 United Kingdom ................. 424/1.1

Primary Examiner—Christine M. Nucker
Attorney, Agent, or Firm—Finnegan, Henderson, Farabow, Garrett & Dunner

[57] ABSTRACT

N-(4-Aminobenzoyl)-aspartic acid and -glutamic acid, their physiologically acceptable salts or their esters are described as stabilizers for Tc$^{99m}$ injection preparations which contain a tin-II compound as a reducing component and an organ-specific component, as well as the production of such injection preparations for bone scintigraphy.

3 Claims, No Drawings

N-(4-AMINOBENZOYL)-AMINODICARBOXYLIC ACIDS FOR STABILIZING TECHNETIUM$^{99m}$ PREPARATIONS, STABILIZED INJECTION PREPARATIONS, AND PROCESSES FOR PRODUCING THEM

The present invention relates to substances, by means of which technetium$^{99m}$-containing injection solutions, which are used for bone scintigraphy, can be stabilized.

In nuclear-medical diagnostics, technetium$^{99m}$ has become the most important radio nuclide, due to its favorable physical properties (short half life of 6 hours, $\gamma$ energy of 140 keV and absence of corpuscular radiation) and the consequent low radiation exposure.

Technetium$^{99m}$, which can be obtained from nuclide generators, is initially present as the pertechnetate which is suitable for scintigraphic recording of the thyroid and the brain. The scintigraphy of other organs by means of technetium$^{99m}$ is possible with the aid of certain "transport substances" which are capable, on the one hand, of binding technetium and, on the other hand, of enriching the radio nuclide with high selectivity in the target organ. For labelling this organ-specific "transport substance" with technetium$^{99m}$, the pertechnetate eluted from the nuclide generator must first be converted to a lower oxidation stage. In this reduced form, technetium forms more or less stable compounds with the organ-specific substance. The reduction of the pertechnetate ($TcO_4^-$) is effected either by chemical reducing agents or by electrolysis methods. In practice, tin-II salts, such as tin-II chloride, fluoride, oxide or tartrate, are used almost exclusively, the chloride being particularly preferred.

In general, the tin-II salt is present together with the organ-specific substance in the lyophilized form, whereby these preparations can be preserved and can be stored unchanged for many months. In the hospital, the user then only has to add a sterile solution, eluted from the nuclide generator, of the pertechnetate with the required Tc$^{99m}$ activity, in order to produce the Tc$^{99m}$-labelled injection preparation.

In contrast to the as yet unlabelled lyophilized product, comprising the organ-specific substance and tin-II salt, these injection solutions have a life of only a few hours. This is due less to the relatively short half life of technetium$^{99m}$ than to the stability of the tin-II ions in the solution. It is known that tin-II compounds are relatively rapidly hydrolyzed in a neutral aqueous solution. Since the injection solutions should be physiologically tolerated, their pH value is in general between 5 and 8, i.e. in a range in which tin-II is not particularly stable.

In the Tc$^{99m}$ preparations, however, there must always be an excess of the organ-specific substance over the tin-II acting as the reducing agent, since the diagnostic applicability of the radiopharmacon is decisively affected by the quantitative ratio of the components. If the tin-II content in a labelling unit is too high, it is possible that, under some circumstances, not all the tin is bonded in a complex any longer, and technetium which is reduced but not bonded to the active ingredient is formed. This contamination, called a "colloid", is produced due to sparingly soluble tin hydroxide, which is present in a colloidal form, being formed from tin ions at the pH value of the eluates, which as a rule is between 5 and 6. The technetium dioxide produced by the reduction under these conditions precipitates together with the tin hydroxide, and this leads to increased enrichment of technetium$^{99m}$ in the liver and spleen.

Conversely, if the quantity of tin-II in the injection solution were insufficient, pertechnetate would still be present, and this can interfere with the scintigraphic representation of the organ, due to enrichment in the stomach and in the thyroid. The following approximate calculation shows that, in one Tc$^{99m}$ labelling unit, a sufficiently large excess of tin-II is usually present by means of which the added pertechnetate is quantitatively reduced. 37 MBq (1 mCi) of Tc$^{99m}$ contain about $10^{12}$ atoms, corresponding to a quantity of $1.92 \times 10^{-6}$ $\mu$mol or 190 pg. If it is assumed that, depending on the preparation, 185–7,400 MBq (5–200 mCi) are used in labelling, the chemical reactions take place with technetium quantities of a few ng.

10 ml of generator eluate having an activity concentration of 740 MBq (20 mCi) per ml are added to the labelling unit, described in European Patent 0,002,485, for scintigraphy of the skeleton, which unit comprises 13 mg of tetrasodium 3,3-diphosphono-propane-1,2-dicarboxylate as the organ-specific substance and 0.2 mg of tin-II as the reducing agent. With the 7,400 MBq (200 mCi), the solution ready for injection thus contains $4 \times 10^{-4}$ $\mu$mol or 40 ng of Tc$^{99m}$. However, the technetium$^{99m}$ obtained from a nuclide generator is not carrier-free since, on the one hand, 14% of molybdenum$^{99}$ decay directly to Tc$^{99}$ and, on the other hand, Tc$^{99}$ is continuously produced by radioactive decay from the Tc$^{99m}$ formed. With daily elution, about 2.5 atoms of Tc$^{99}$ are still present per atom of Tc$^{99m}$, and these participate in all chemical processes in the same way as Tc$^{99m}$. This means that a part of the tin-II in the labelling unit is consumed for the reduction of the Tc$^{99m}$ pertechnetate which cannot be utilized diagnostically.

In the above example, the three components of the radiopharmacon ready for injection, namely technetium (1.4 nmol), tin (1.7 $\mu$mol) and tetrasodium 3,3-diphosphono-propane-1,2-dicarboxylate (34 $\mu$mol) are accordingly present in a molar ratio of 1:1,200:24,000. Since 3 atoms of tin-II per 2 atoms of Tc-VII are required for the reduction of the pertechnetate to positively 4-valent technetium, the 0.2 mg of tin-II present in the labelling unit represents an 800-fold excess.

This large excess of tin-II over technetium, which is the rule in almost all Tc$^{99m}$ preparations, guarantees an injection solution which is free from $TcO_4^-$ and which, in most cases, is also stable for several hours. The presence of tin-II in the solution is a precondition for the stability of the Tc$^{99m}$ injection preparation. If, however, the tin-II in the injection solution is consumed by hydrolysis after a standing period of greater or lesser duration, pertechnetate can be formed again in the solution by reoxidation from the reduced technetium under the action of small quantities of atmospheric oxygen.

Attempts have been made to prevent reoxidation of the technetium in injection preparations by the addition of antioxidants. Thus, for example ascorbic acid, gentisic acid or nitrite have been suggested for the stabilization of Tc$^{99m}$ preparations (cf. e.g. German Offenlegungsschrift No. 2,618,337, and Europeaun Patent Applications carrying the publication numbers Nos. 0,004,684 and 0,046,067). From these, gentisic acid and ascorbic acid are already being used as stabilizing additives in some commercial preparations.

Investigations with these substances have shown, however, that their effectiveness is low when hgh $Tc^{99m}$ activity concentrations are used. Some $Tc^{99m}$ preparations, above all the diphosphonates used for scintigraphy of the skeleton, are offen labelled using high activity concentrations. Attempts are made to reduce the costs per examination by distributing the contents of one labelling unit over the greatest possible number of patients. For this purpose, high $Tc^{99m}$ activities per labelling unit must be added, and a longer application period of the injection solution, if possible over a full working day, is desired.

As shown by extensive investigations in our laboratories, the stability of a $Tc^{99m}$ injection solution decreases when increasing $Tc^{99m}$ activities are added. Thus, in the case of the abovementioned bone diagnostic agent, namely 3,3-diphosphono-propane-1,2-dicarboxylic acid (DPD), it was found (Table 1) that, with the addition of 3,700 MBq (100 mCi) per labelling unit, sufficient tin-II ions for preventing the appearance of pertechnetate in the solution were still present after a standing period of 8 hours. By contrast, it was found that, when 14,800 MBq (400 mCi) in 5 ml of generator eluate were used, all the tin-II was already consumed 5 hours after the preparation and, naturally, free pertechnetate was detectable in the solution.

TABLE 1

Influence of the added activity quantity of $Tc^{99m}$ on the tin-II content and the pertechnetate proportion in the 3,3-diphosphono-propane-1,2-dicarboxylic acid (DPD) labelling unit as a function of the time after preparation, with 5 ml of eluate in each case

| MBq | Tin-II content (*) after preparation (hours) in μg | | | | Pertechnetate proportion (**) in the solution after preparation (hours) in % | | | |
|---|---|---|---|---|---|---|---|---|
| | 0 | 2 | 5 | 8 | 0 | 2 | 5 | 8 |
| 1,850 | 200 | 168 | 137 | 108 | <1 | <1 | <1 | <1 |
| 3,700 | 200 | 152 | 119 | 88 | <1 | <1 | <1 | <1 |
| 7,400 | 200 | 136 | 84 | 30 | <1 | <1 | <1 | 2 |
| 11,100 | 200 | 115 | 48 | <10 | <1 | <1 | <1 | 4 |
| 14,800 | 200 | 96 | <10 | — | <1 | <1 | 3 | 8 |

(*) Tin-II determination by iodometric titration
(**) Measurement of the $Tc^{99m}$ pertechnetate proportion by paper chromatography (Whatman Paper No. 1; Methanol:Water = 8:2)

Under the influence of high $Tc^{99m}$ activities, an accelerated radiochemical oxidation of the reducing tin-II ions occurs in the injection solution. During the search for more effective stabilizers, the substituted aminodicarboxylic acids N-(4-aminobenzoyl)-L-aspartic acid and N-(4-aminobenzoyl)-L-glutamic acid were, surprisingly, found to be substances, by means of which even injection solutions containing high $Tc^{99m}$ activity concentrations can be preserved for a longer period after they have been prepared.

The invention therefore relates to N-(4-aminobenzoyl)-aspartic and -glutamic acid, to their physiologically acceptable salts and to their esters as stabilizers for $Tc^{99m}$ injection preparations for bone scintigraphy, which preparations contain tin-II compounds, and to processes for producing stabilized, $Tc^{99m}$-labelled radiodiagnostic agents, wherein N-(4-aminobenzoyl)-aspartic acid or -glutamic acid or their esters are added as additional components either to the inactive labelling unit or, together with the technetium$^{99m}$ pertechnetate solution, to the substance to be labelled.

When the stabilizer is added to the inactive labelling unit, the stabilizer is either added to the mixture of organ-specific component and tin-II compound before filling and portions of the solution obtained are filled into containers and lyophilized, or the lyophilized content of a filled container (labelling unit) is first dissolved in stabilizer-containing physiological saline and then labelled by adding the $Tc^{99m}$ pertechnetate solution. Since the organ distribution of the technetium$^{99m}$ preparation can be changed by an unduly high proportion of the stabilizer component, it is advantageous not to exceed a molar tin-II/stabilizer ratio of 1:10. Distribution studies on rats have shown that, with a molar tin-II/N-(4-aminobenzoyl)-L-glutamic acid ratio of 1:10 to 1:30, these compounds being added as reducing and stabilizing components to the bone-specific $Tc^{99m}$ diphosphono-propane-1,2-dicarboxylic acid (DPD), the storage of this $Tc^{99m}$ complex in the skeleton was markedly reduced at the expense of increased renal excretion.

A molar tin-II/N-substituted aminodicarboxylic acid ratio of 1:2 to 1:6 is the optimum, and is sufficient for stabilization even if very high $Tc^{99m}$ activities (up to 18,500 MBq) are added, so that a filled container (labelling unit), suitable for administration to humans, logically contains 0.85–2.7 mg of stabilizer in addition to the organ-specific substance, if the reducing agent ($Sn^{2+}$) likewise contained therein is present in a quantity of about 0.2 mg.

The stabilizers used according to the invention for producing a labelling unit are either N-(4-aminobenzoyl)aspartic acid or N-(4-aminobenzoyl)-glutamic acid, and more advantageously their sodium salts, since these are more easily soluble in water. In addition, the dimethyl or diethyl esters of N-(4-aminobenzoyl)-aspartic or -glutamic acid are also suitable.

EXAMPLE 1

1 ml of physiological NaCl solution (pH~7), in which 2 mg of sodium N-(4-aminobenzoyl)-L-glutamate are dissolved, is added to 4 ml of pertechnetate solution, which contain 14,800 MBq (400 mCi) of $Tc^{99m}$. This solution is added to a lyophilized labelling unit, comprising 13 mg of tetrasodium 3,3-diphosphono-propane-1,2-dicarboxylate and 0.2 mg of tin-II. After standing for 16 hours, the solution is diluted with physiological NaCl solution to a concentration of 0.26 mg of diphosphonate/ml, and 0.05 ml (13 μg) per rat is administered intravenously in each case. In parallel, the same preparation, but without added N-(4-aminobenzoyl)-L-glutamic acid as a stabilizer, is labelled with 14,800 MBq of $Tc^{99m}$ and diluted after the same standing period, and the product is injected in an analogous concentration into rats.

The organ distribution in 3 rats was determined in each case 2 hours after injection. The following values (n percent of the dose administered, see Table 2) show the clear difference in organ distribution between the stabilizer-containing and the stabilizer-free $Tc^{99m}$ preparations, the increased enrichments in the stomach and thyroid indicating the presence of pertechnetate in the injection solution.

TABLE 2

| | $Tc^{99m}$ DPD | |
|---|---|---|
| | with stabilizer | without stabilizer |
| Bone/g | 4.22 | 3.92 |
| Blood/ml | 0.015 | 0.068 |
| Muscle/g | 0.005 | 0.040 |
| Liver | 0.22 | 0.58 |
| Lungs | 0.058 | 0.096 |
| Kidneys | 0.44 | 1.20 |
| Intestines | 1.11 | 3.26 |
| Stomach | 0.29 | 2.86 |
| Thyroid | 0.017 | 0.061 |

EXAMPLE 2

A labelling unit comprising 7.2 mg of sodium pyrophosphate and 1.08 mg of SnCl$_2$ is dissolved in 2 ml of physiological NaCl solution (pH~7) which contains sodium N-(4-aminobenzoyl)-L-aspartate in a concentration of 1 mg/ml. Immediately afterwards, 8 ml of pertechnetate solution with 12,950 MBq (350 mCi) are added, and samples are then taken at defined intervals from the labelling batch and are tested for free pertechnetate by paper chromatography. The test is carried out on Whatman-1 paper, using methanol:water=8:2 (Vol/Vol) as the mobile phase. The pertechnetate separated off with an Rf value of 0.6 from Tc$^{99m}$ pyrophosphate (Rf=0) is determined by means of a radiochromatograph. A pyrophosphate which was labelled under the same conditions but to which no stabilizer was added, already contains pertechnetate after a relatively short period of standing, as can be seen from Table 3:

TABLE 3

| Time after preparation (hours) | % of pertechnetate in Tc$^{99m}$ pyrophosphate with stabilizer | without stabilizer |
|---|---|---|
| 0.5 | <1 | <1 |
| 2 | <1 | <1 |
| 4 | <1 | 1 |
| 6 | <1 | 3 |
| 8 | <1 | 7 |
| 12 | <1 | 10 |

EXAMPLE 3

2 g of methylenediphosphonic acid (MDP) and 268 mg of diethyl N-(4-aminobenzoyl)-L-glutanate are dissolved together in 3 ml of twice-distilled water, and the pH value of the solution is adjusted to 6.5 by means of about 27 ml of 1N sodiumhydroxide solution. With exclusion of air, 56 mg of tin-II oxide are added to the solution. After the SnO has completely dissolved, the solution is diluted with 70 ml of water and the sterile-filtered solution is distributed in 0.5 ml portions over small rolled-rim bottles pre-frozen with liquid nitrogen and is freeze-dried. The filled containers are blanketed with nitrogen and sealed.

Samples investigated by iodometric titration showed an unchanged content of 0.2 mg of tin-II per filled container after several weeks' storage. The preparation, to which Tc$^{99m}$ pertechnetate solutions of high activity concentrations had been added, was free from pertechnetate even after standing for 8 hours and was suitable for scintigraphic representation of the skeleton.

EXAMPLE 4

90 mg of ultra-pure tin-II oxide is dissolved at room temperature in 26 ml of 2N sodiumhydroxide solution under air-free conditions. A solution containing 4 g of 3,3-diphosphono-propane-1,2-dicarboxylic acid (DPD) and 356 mg of N-(4-aminobenzoyl)-1-aminoglutamic acid in 20 ml of twice-distilled water is allowed to run into the sodium stannite solution with stirring. The clear solution is diluted with sterile water to a total volume of 200 ml and then filled in 0.5 ml portions into small rolled-rim bottles pre-cooled with liquid nitrogen. After freeze-drying, the small glass bottles are sealed in vacuo.

Animal experiments were carried out with the Tc$^{99m}$ DPD, as described in Example 1, the following results being obtained after 16 hours' standing of the injection solutions and 2 hours after the intravenous administration of the preparation (in % of the dose administered):

| Bone | Liver | Kidneys | Thyroid | Stomach | Blood |
|---|---|---|---|---|---|
| 45.3 | 0.26 | 0.77 | 0.018 | 0.22 | 0.36 |

I claim:

1. A composition useful as an injection preparation for bone scintigraphy comprising, in solution, Tc$^{99m}$ pertechnetate, a tin-II compound reducing component, an organ-specific substance and at least one Tc$^{99m}$ stabilizer selected from the group consisting of N-(4-aminobenzoyl)aspartic acid, N-(4-aminobenzoyl)-glutamic acid, the physiologically acceptable salts of said acids and the esters thereof of said acids.

2. A composition useful as an injection preparation for bone scintigraphy comprising, in solution, Tc$^{99m}$ pertechnetate, a tin-II compound reducing component, an organ-specific substance and a Tc$^{99m}$ stabilizer selected from the group consisting of N-(4-aminobenzoyl)-aspartic acid, a physiologically acceptable salt of said acid, and the dimethyl and diethyl esters of said acid.

3. A composition useful as an injection preparation for bone scintigraphy comprising, in solution, Tc$^{99m}$ pertechnetate, a tin-II compound reducing component, an organ-specific substance and a Tc$^{99m}$ stabilizer selected from the group consisting of N-(4-aminobenzoyl)-glutamic acid, a physiologically acceptable salt of said acid, and the dimethyl and diethyl esters of said acid.

* * * * *